017
United States Patent [19]

McCall

[11] Patent Number: 4,487,774
[45] Date of Patent: Dec. 11, 1984

[54] ISOCHROMANS

[75] Inventor: John M. McCall, Kalamazoo, Mich.

[73] Assignee: The Upjohn Company, Kalamazoo, Mich.

[21] Appl. No.: 370,327

[22] Filed: Apr. 21, 1982

Related U.S. Application Data

[63] Continuation of Ser. No. 026,719, Apr. 4, 1979, , which is a continuation-in-part of Ser. No. 847,350, Oct. 31, 1977, abandoned.

[51] Int. Cl.$^3$ ............... A61K 31/445; C07D 405/06; C07D 405/14
[52] U.S. Cl. .................. 424/256; 424/248.57; 424/249; 424/250; 424/251; 424/258; 424/267; 424/283; 544/151; 544/376; 544/378; 546/148; 546/196; 546/199; 546/269; 549/387; 549/399; 549/407
[58] Field of Search ............ 544/376, 151, 378; 424/248.57, 249, 250, 251, 256, 258, 267, 283; 546/148, 196, 199, 269; 549/387, 399, 407

[56] References Cited

U.S. PATENT DOCUMENTS 3,467,675 9/1969 Petersen et al. .................. 544/376

Primary Examiner—Paul M. Coughlan, Jr.
Attorney, Agent, or Firm—Joan Thierstein

[57] ABSTRACT

Amino derivatives of isochromans are described. These compounds exhibit antipsychotic and hypotensive activity.

63 Claims, No Drawings

ISOCHROMANS

CROSS REFERENCE TO RELATED APPLICATION

This is a continuation of application Ser. No. 026,719, filed Apr. 4, 1979, which is a continuation-in-part of copending application Ser. No. 847,350, filed Oct. 31, 1977, now abandoned.

SUMMARY OF THE INVENTION

The present application relates to novel compounds which are amines of certain isochromans. In particular the present invention relates to the novel isochromans disclosed in U.S. Ser. No. 858,303, now U.S. Pat. No. 4,153,612, the disclosure of which is incorporated here by reference.

In particular, U.S. Ser. No. 858,303 describes the use of certain isochromans as intermediates for preparing isochroman amine type compounds. With respect to the specification of U.S. Ser. No. 858,303, particular reference is made to Tables 14 and 15 therein.

Moreover, the examples 20, 21a, 21b and 21c provide examples of preparation of amines according to formulas of Tables 14 and 15 therein. Accordingly, there are described:

4-(4-chlorophenyl)-1-[(3,4-dihydro-6,7-dimethoxy-4,4-dimethyl-1H-2-benzopyran-1-yl)meth yl]-1,2,3,6-tetrahydropyridine, monohydrochloride in Example 20;

1-[3-(3,4-dihydro-6,7-dimethoxy-1-methyl-1H-2-benzopyran-1-yl)propyl]-4-(4-fluorophenyl)-piperazine, dihydrochloride in Example 21a;

1-[2-(6,7-dimethoxy-4,4-dimethylisochroman-1-yl)ethyl]-4-(3-trifluoromethylphenyl)piperazine, dihydrochloride in Example 21b; and 2-[2-[(6,7-dimethoxy-4,4-dimethylisochroman-1-yl)ethyl]]-6,7-dimethoxy-1,2,3,4-tetrahydroisoquinoline monohydrochloride in Example 21c.

As indicated in the text associated with Table 14 in U.S. Ser. No. 858,303, the method of preparing the isochroman amine type compounds of Table 14 is in the manner of Examples 20, 21a and 21b from the appropriate (6,7-dimethoxy-isochroman-1-yl)alkyl halides and the appropriate amines. Likewise, certain additional isochroman amine type compounds represent novel chemical entities comprising one aspect of the present invention. Moreover, these novel compounds are prepared by following procedures similar to those of Examples 20, 21a and 21b in U.S. Ser. No. 858,303, but substituting the appropriate (6,7-dimethoxyisochroman-1-yl)alkyl halides and the appropriate amines. (Table I).

TABLE I

| HNR$_9$R$_{10}$ | n | R$_2$ | R$_3$ | R$_8$ | °C./Hrs. | Misc. | M.P. (°C.) | Anal. (Found) | Name |
|---|---|---|---|---|---|---|---|---|---|
| H—N⟨piperidine⟩—⟨phenyl⟩ (with double bond) | 3 | H | H | CH$_3$ | | | 197–199$^a$ | | 4-Phenyl-1-[3-(3,4-dihydro-6,7-dimethoxy-1-methyl-1H—2-benzopyran-1-yl)propyl]-1,2,3,6-tetrahydropyridine. |
| H—N⟨piperazine⟩—N—⟨2-Cl-phenyl⟩ | 2 | H | CH$_3$ | H | | | 170–172$^d$ decomposes | | 4-(2-chlorophenyl)-1-[2-(3,4-dihydro-6,7-dimethoxy-4-methyl-1H—2-benzopyran-1-yl)ethyl]piperazine. |
| H—N⟨piperazine⟩—N—⟨2-pyridyl⟩ | 3 | H | H | CH$_3$ | | | 230–231° C. | as mono MeOH.HCl C, 58.31; H, 7.10; N, 8.14; Cl, 13.75 | 4-(2-pyridyl)-1-[3-(3,4-dihydro-1-methyl-6,7-dimethoxy-1H—2-benzopyran-1-yl)propyl]piperazine. |
| H—N⟨piperazine⟩—N—⟨phenyl⟩ | 2 | CH$_3$ | H | H | | | 190–191$^d$ | C, 50.95; H, 7.32; N, 6.22; Cl, 14.86 | 4-phenyl-1-[2-(3,4-dihydro-6,7-dimethoxy-4-methyl-1H—2-benzopyran-1-yl)ethyl]piperazine. |
| H—N⟨tetrahydropyridine⟩—⟨phenyl⟩ | 2 | CH$_3$ | H | H | | | 202–204$^a$ | C, 69.49; H, 7.63; N, 2.98; Cl, 8.35 | 4-phenyl-1-[2-(3,4-dihydro-6,7-dimethoxy-4-methyl-1H—2-benzopyran-1-yl)ethyl]-1,2,3,6-tetrahydropyridine. |
| H—N⟨piperazine⟩—N—⟨phenyl⟩ | 3 | CH$_3$ | CH$_3$ | CH$_3$ | | | 225–227$^d$ | C, 63.79; H, 7.93; N, 5.53; Cl, 13.01 | 4-phenyl-1-[3-(3,4-dihydro-6,7-dimethoxy-1,4,4-trimethyl-1H—2-benzopyran-1-yl)propyl]piperazine. |

TABLE I-continued

[Structure: dimethoxybenzopyran with substituents R2, R3, R8, and (CH2)nNR9R10 side chain]

| HNR9R10 | n | R2 | R3 | R8 | °C./Hrs. | Misc. | M.P. (°C.) | Anal. (Found) | Name |
|---|---|---|---|---|---|---|---|---|---|
| H–N(piperidine)–phenyl (tetrahydropyridine) | 3 | $CH_3$ | $CH_3$ | $CH_3$ | | | 221–223[b] | C, 70.43; H, 7.80; N, 2.93; Cl, 7.70 | 4-phenyl-1-[3-(3,4-dihydro-6,7-dimethoxy-1,4,4-trimethyl-1H—2-benzopyran-1-yl)propyl]-1,2,3,6-tetrahydropyridine. |
| H–N(piperazine)–N–(2-methylphenyl) | 3 | $CH_3$ | $CH_3$ | $CH_3$ | | | 223–225[a] | C, 68.44; H, 8.28; N, 5.47; Cl, 7.02 | 4-(2-methylphenyl)-1-[3-(3,4-dihydro-6,7-dimethoxy-1,4,4-trimethyl-1H—2-benzopyran-1-yl)propyl]piperazine. |
| H–N(tetrahydropyridine)–phenyl | 3 | $CH_3$ | $CH_3$ | 4-F-phenyl | | | 112–115[c] | C, 69.21; H, 7.36; N, 2.48; Cl, 6.66 | 4-phenyl-1-[3-[1-(4-fluorophenyl)-3,4-dihydro-6,7-dimethoxy-4,4-dimethyl-1H—2-benzopyran-1-yl]propyl]-1,2,3,6-tetrahydropyridine. |
| H–N(piperazine)–N–(4-fluorophenyl) | 3 | $CH_3$ | $CH_3$ | $CH_3$ | | | 231–233[g] | C, 60.72; H, 7.30; H, 5.14; Cl, 12.91; F, 5.24 | 4-(4-fluorophenyl)-1-[3-(3,4-dihydro-6,7-dimethoxy-1,4,4-trimethyl-1H—2-benzopyran-1-yl)propyl]piperazine. |
| H–N(piperazine)–N–phenyl | 3 | $CH_3$ | $CH_3$ | 4-F-phenyl | | | 225–227[c] | C, 66.86; H, 7.21; N, 4.97; Cl, 7.17; F, 3.22 | 4-phenyl-1-[3-[1-(4-fluorophenyl)-3,4-dihydro-6,7-dimethoxy-4,4-dimethyl-1H—2-benzopyran-1-yl]propyl]piperazine. |
| HN(tetrahydropyridine)–phenyl | 3 | $CH_3$ | H | 4-F-phenyl | | | 220–223[a] | C, 71.06; H, 6.96; N, 2.91; Cl, 6.56; F, 3.52 | 4-phenyl-1-[3-[1-(4-fluorophenyl)-3,4-dihydro-6,7-dimethoxy-4-methyl-1H—2-benzopyran-1-yl]propyl]-1,2,3,6-tetrahydropyridine. |
| HN(tetrahydropyridine)–phenyl | 3 | $CH_3$ | H | $CH_3$ | | | 187–189[b] | C, 69.91; H, 7.55; N, 3.14; Cl, 8.03 | 4-phenyl-1-[3-(3,4-dihydro-6,7-dimethoxy-1,4-dimethyl-1H—2-benzopyran-1-yl)propyl]-1,2,3,6-tetrahydropyridine. |
| HN(piperazine)–N–phenyl | 3 | $CH_3$ | H | 4-F-phenyl | | | 254–256[a] | C, 68.66; H, 7.12; N, 5.09; Cl, 6.76; F, 3.52 | 4-phenyl-1-[3-[1-(4-fluorophenyl)-3,4-dihydro-6,7-dimethoxy-4-methyl-1H—2-benzopyran-1-yl]propyl]piperazine. |
| HN(piperazine)–N–(2-methylphenyl) | 3 | $CH_3$ | H | $CH_3$ | | | 209–211[a] | C, 67.70; H, 8.26; N, 6.32; Cl, 7.55 | 4-(2-methylphenyl)-1-[3-(3,4-dihydro-6,7-dimethoxy-1,4-dimethyl-1H—2-benzopyran-1-yl)propyl]piperazine. |
| H–N(piperazine)–N–(2-chlorophenyl) | 2 | $CH_3$ | $CH_3$ | H | | | 148–149.5[d] | C, 57.29; H, 6.92; N, 5.61; Cl, 20.48 | 4-(2-chlorophenyl)-1-[2-(3,4-dihydro-6,7-dimethoxy-4,4-dimethyl-1H—2-benzopyran-1-yl)ethyl]piperazine. |
| H–N(piperazine)–N–(3-chlorophenyl) | 2 | $CH_3$ | $CH_3$ | H | | | 161–165[a] | C, 61.82; H, 7.09; N, 5.63; Cl, 15.24 | 4-(3-chlorophenyl)-1-[2-(3,4-dihydro-6,7-dimethoxy-4,4-dimethyl-1H—2-benzopyran-1-yl)ethyl]piperazine. |

TABLE I-continued

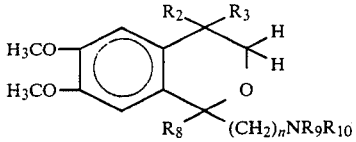

| HNR9R10 | n | R2 | R3 | R8 | °C./Hrs. | Misc. | M.P. (°C.) | Anal. (Found) | Name |
|---|---|---|---|---|---|---|---|---|---|
| 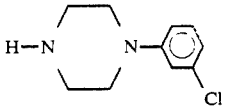 | 2 | CH3 | H | H | | | 115.5–117 | C, 66.65; H, 7.30; N, 6.42; Cl, 8.24 | 4-(3-chlorophenyl)-1-[2-(3,4-dihydro-6,7-dimethoxy-4-methyl-1H—2-benzopyran-1-yl)ethyl]piperazine. |
| 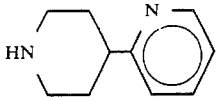 | 3 | H | H | CH3 | | | | | 4-(2-pyridyl)-1-[3-(3,4-dihydro-1-methyl-6,7-dimethoxy-1H—2-benzopyran-1-yl)propyl]piperidine. |
| 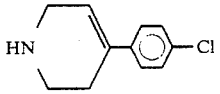 | 2 | CH3 | CH3 | H | | | | | 4-(4-chlorophenyl)-1-[2-(3,4-dihydro-6,7-dimethoxy-4,4-dimethyl-1H—2-benzopyran-1-yl)ethyl]-1,2,3,6-tetrahydropyridine. |
| 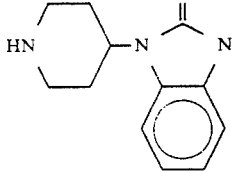 | 2 | CH3 | CH3 | H | | | | | 1-[2-(3,4-dihydro-6,7-dimethoxy-4,4-dimethyl-1H—2-benzopyran-1-yl)ethyl]piperidin-4-yl]-1,3-dihydro-2H—benzimidazol-2-one. |

[a] HCl salt
[b] HCl salt hemihydrate
[c] HCl salt hydrate
[d] dihydrochloride salt
[e] dihydrate
[f] trihydrate hydrochloride
[g] dihydrochloride, hemihydrate

TABLE II

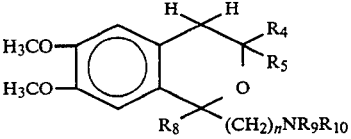

| HNR9R10 | n | R4 | R5 | R8 | °C./Hrs. | Misc. | M.P.(°C.) | Anal. (Found) | Name |
|---|---|---|---|---|---|---|---|---|---|
| 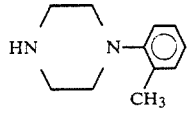 | 2 | CH3 | CH3 | H | | | 222–223[a] | C, 67.77; H, 8.02; N, 6.01 | 4-(2-methylphenyl)-1-[2-(3,4-dihydro-6,7-dimethoxy-3,3-dimethyl-1H—2-benzopyran-1-yl)ethyl]piperazine. |
| 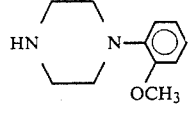 | 2 | CH3 | CH3 | H | | | 187–189[d] | C, 60.86; H, 7.68; N, 5.51; Cl, 12.76 | 4-(2-methoxyphenyl)-1-[2-(3,4-dihydro-6,7-dimethoxy-3,3-dimethyl-1H—2-benzopyran-1-yl)ethyl]piperazine. |
| 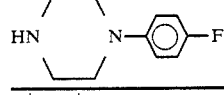 | 2 | CH3 | CH3 | H | | | 161–163[b] | C, 63.20; H, 7.16; N, 6.18 | 4-(4-fluorophenyl)-1-[2-(3,4-dihydro-6,7-dimethoxy-3,3-dimethyl-1H—2-benzopyran-1-yl)ethyl]piperazine. |

[a], [b], and [d] are as defined for TABLE I.

Compounds of Tables I and II above are within the preferred compounds of U.S. Ser. No. 858,303, Formula I'. Compounds within this group having an alkyl group of one through three carbons at one of the positions $R_2$ through $R_5$ or $R_8$ are more preferred. Further, new compounds of this invention, i.e. 4-(2-chlorophenyl)-1-[2-(3,4-dihydro-6,7-dimethoxy-4,4-dimethyl-1H-2-benzopyran-1-yl)ethyl]piperazine and 4-(3-chlorophenyl-1-[2-3,4-dihydro-6,7-dimethoxy-4,4-dimethyl-1H-2-benzopyran-1-yl)ethyl]piperazine are among those specifically preferred compounds of Formula I' as defined in U.S. Ser. No. 858,303. In addition compounds prepared herein having alkyls of from one to three carbon atoms, inclusive, at the $R_4$ and $R_5$ positions of Formula I', wherein b is zero and $R_8$ is hydrogen are now also found to be among those specifically preferred in the present invention.

Further, the present invention now comprises the unexpected discovery that certain of the isochroman amine type compounds of U.S. Ser. No. 858,303 and Tables I and II of this disclosure exhibit a split in activity between an antipsychotic and a hypotensive effect. In other words, such compounds have either first, a high antipsychotic and low cardiovascular effect or second, a low antipsychotic and high cardiovascular effect. The effect of the first split recited above is exhibited by 4-phenyl-1-[2-(3,4-dihydro-6,7-dimethoxy-4,4-dimethyl-1H-2-benzopyran-1-yl)ethyl]-1,2,3,6-tetrahydropyridine monohydrochloride hemihydrate, listed as the eighth compound in Table 14 of U.S. Ser. No. 858,303, 4-phenyl-1-[2-(3,4-dihydro-6,7-dimethoxy-4-methyl-1H-2-benzopyran-1-yl)ethyl]-1,2,3,6-tetrahydropyridine and 4-(2-chlorophenyl)-1-[2-(3,4-dihydro-6,7-dimethoxy-4-methyl-1H-2-benzopyran-1-yl)ethyl]-piperazine, the latter compounds are included in Table I herein. The effect of the second split recited above is exhibited by 4-phenyl-1-[3-(3,4-dihydro-6,7-dimethoxy-1-methyl-1H-2-benzopyran-1-yl)propyl]-1,2,3,6-tetrahydropyridine, 4-phenyl-1-[3-(3,4-dihydro-6,7-dimethoxy-1,4,4-trimethyl-1H-2-benzopyran-1-yl)propyl]-1,2,3,6-tetrahydropyridine, 4-phenyl-1-[3-[1-(4-fluorophenyl)-3,4-dihydro-6,7-dimethoxy-4,4-dimethyl-1H-2-benzopyran-1-yl]-propyl]-1,2,3,6-tetrahydropyridine and 4-phenyl-1-[3-(3,4-dihydro-6,7-dimethoxy-1,4-dimethyl-1H-2-benzopyran-1-yl)propyl]-1,2,3,6-tetrahydropyridine, all shown in Table I above.

In the formulation of compounds in the present invention for pharmacological utility conventional techniques are used as fully disclosed in U.S. Ser. No. 858,303.

I claim:
1. Compounds having the formula

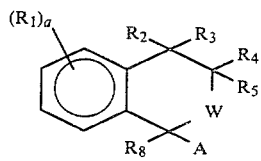
Ib wherein
$R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;
a is one through three;
$R_2$ through $R_5$ are the same or different and are selected from the group consisting of hydrogen, alkyl of one through three carbons, inclusive, hydroxy, alkoxy of one through three carbons, inclusive; phenyl; halo; cycloalkyl of three through six carbons when $R_2$ and $R_3$ or $R_4$ and $R_5$ are taken together with the carbon to which they are attached; cycloalkyl of four through seven carbons when $R_2$ and $R_4$ are taken together with the carbons to which they are attached; and cycloalkyl of five or six carbons, with the overall provisos that no more than one ring may be attached to any one carbon and that at least two of $R_2$ through $R_5$ are hydrogen,
$R_8$ is alkyl of one through three carbons, inclusive, hydrogen, or phenyl unsubstituted or substituted with a maximum of three substituents selected from the group consisting of alkyl of one through three carbons, inclusive, halo, alkoxy of one through three carbons, inclusive, and trihaloalkyl of one to two carbons;
W is oxygen; and A is selected from the group consisting of:
(i) —$(CH_2)_n NR_9 R_{10}$, wherein n is one to five with the proviso that when n is one or two, $R_2$ through $R_5$ cannot all be hydrogen at the same time;
(ii) —$(CH_2)_m(OCH_2CH_2)_q$—$NR_{21}R_{22}$, wherein m and q are each one to three, and $NR_{21}R_{22}$ is selected from the group consisting of —$NHCH_2CH_2Ar$; $NR_{21}'R_{22}'$ wherein $R_{21}'$ and $R_{22}'$ can be the same or different and are selected from the group consisting of H, alkyl of one through four carbons, inclusive, and together with the N to which they are attached form heterocyclic rings of four to six ring atoms; and

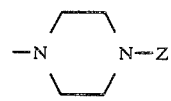

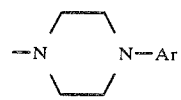

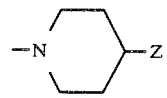

morpholino and $NR_9R_{10}$,

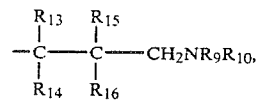 (iii)

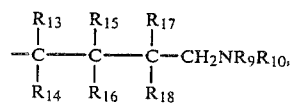 (iv)

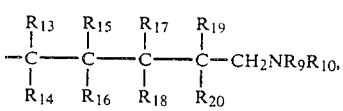 (v)

wherein

NR$_9$R$_{10}$ is a heterocyclic amine selected from the group consisting of:

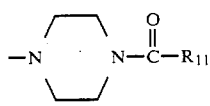

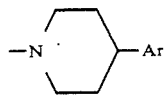

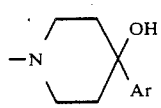

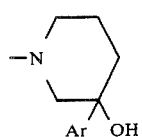

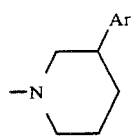

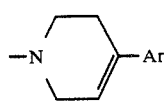

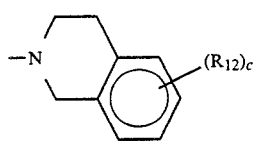

and

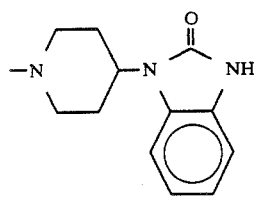

wherein

R$_{11}$ is alkyl of one through four carbons, inclusive, 2-furyl, Ar, alkoxy of one to three carbon atoms, inclusive;

Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive;

R$_{12}$ is alkyl or alkoxy of one through three carbons, inclusive, hydroxy, halo, or trihalomethyl; R$_{13}$ through R$_{20}$ may be the same or different and are selected from the group consisting of hydrogen and alkyl of from 1 to 2 carbon atoms, inclusive, at least one of R$_{13}$ through R$_{20}$ when present being alkyl;

c is zero through two;

Ar is phenyl unsubstituted or substituted with one through three substituents selected from the group consisting of alkyl or alkoxy of one through three carbons, inclusive, hydroxy, halo, and trihaloalkyl or trihaloalkoxy of one or two carbons and pharmaceutically acceptable acid addition salts thereof.

2. Compounds of claim 1 wherein a is two or three.

3. Compounds of claim 1 wherein A is the group —(CH$_2$)$_n$NR$_9$R$_{10}$.

4. Compounds of claim 3 wherein a is two or three, R$_2$ through R$_5$ are the same or different and are selected from the group consisting of hydrogen, alkyl of one through three carbon atoms, inclusive, and cycloalkyl of four through seven carbon atoms, inclusive, when R$_2$ and R$_4$ are taken together with the carbon atom to which they are attached, with the proviso that when R$_3$ through R$_5$ are hydrogen, R$_2$ cannot be hydrogen.

5. Compounds of claim 4 wherein NR$_9$R$_{10}$ is selected from the group consisting of

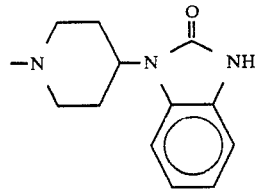

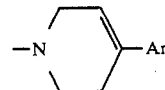

and

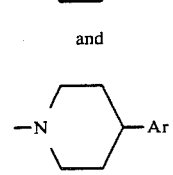

6. A compound of claim 5 wherein (R$_1$)$_a$ is dilower alkoxy of from one to three carbon atoms, inclusive; R$_2$ and R$_3$ are different and are selected from the group consisting of hydrogen and alkyl of from one through three carbons, inclusive and R$_4$ and R$_5$ are both hydrogen.

7. A compound of claim 6 wherein (R$_1$)$_a$ is 6,7-dimethoxy, one of R$_2$ and R$_3$ is methyl and the other is hydrogen, R$_4$ and R$_5$ are hydrogen and NR$_9$R$_{10}$ is 1,2,3,6-tetrahydro-4-phenyl pyridinyl so that the specific embodiment is 4-phenyl-1-[2-(3,4-dihydro-6,7-dimethoxy-4-methyl-1H-2-benzopyran-1-yl)ethyl]-1,2,3,6-tetrahydropyridine.

8. The monohydrochloride of the compound of claim 7.

9. A compound of claim 6 wherein (R$_1$)$_a$ is 6,7-dimethoxy, one of R$_2$ and R$_3$ is methyl and the other is hydrogen, R$_4$ and R$_5$ are hydrogen, R$_8$ is methyl, and NR$_9$R$_{10}$ is 1,2,3,6-tetrahydro-4-phenylpyridinyl so that the specific embodiment is 4-phenyl-1-[3-(3,4-dihydro-6,7-dimethoxy-1,4-dimethyl-1H-2-benzopyran-1-yl)propyl]-1,2,3,6-tetrahydropyridine.

10. The monohydrochloride, hemihydrate of the compound of claim 9.

11. A compound of claim 6 wherein (R$_1$)$_a$ is 6,7-dimethoxy, one of R$_2$ and R$_3$ is methyl and the other is hydrogen, R$_4$ and R$_5$ are hydrogen, R$_8$ is 4-fluorophenyl and NR$_9$R$_{10}$ is 1,2,3,6-tetrahydro-4-phenylpyridinyl so that the specific embodiment is 4-phenyl-1-[3-[1-(4-fluorophenyl)-3,4-dihydro-6,7-dimethoxy-4-methyl-1H-2-benzopyran-1-yl]propyl]-1,2,3,6-tetrahydropyridine.

12. The monohydrochloride of the compound of claim 11.

13. Compounds of claim 5 wherein (R$_1$)$_a$ is a dilower alkoxy of from one to three carbon atoms, inclusive; R$_2$ and R$_2$ are both lower alkyl of from one to three carbon atoms, inclusive; and R$_4$ and R$_5$ are both hydrogen.

14. A compound according to claim 13 wherein (R$_1$)$_a$ is 6,7-dimethoxy, R$_2$ and R$_3$ are both methyl, n is 1, and NR$_9$R$_{10}$ is 4-(4-chlorophenyl)-1,2,3,6-tetrahydropyridinyl so that the specific embodiment is 4-(4-chlorophenyl)-1-[(3,4-dihydro-6,7-dimethoxy-4,4-dimethyl-1H-2-benzopyran-1-yl)methyl]-1,2,3,6-tetrahydropyridine.

15. The monohydrochloride salt of the compound of claim 14.

16. A compound according to claim 13 wherein (R$_1$)$_a$ is 6,7-dimethoxy, R$_2$ and R$_3$ are both methyl and n is 2.

17. A compound according to claim 16 wherein NR$_9$R$_{10}$ is 1,2,3,6-tetrahydro-4-phenylpyridinyl so that the specific embodiment is 1-[2-(3,4-dihydro-6,7-dimethoxy-4,4-dimethyl-1H-2-benzopyran-1-yl)ethyl]-1,2,3,6-tetrahydro-4-phenylpyridine.

18. The monohydrochloride hemihydrate of the compound of claim 17.

19. A compound according to claim 16 wherein NR$_9$R$_{10}$ is 4-(4-chlorophenyl)-1,2,3,6-tetrahydropyridinyl so that the specific embodiment is 4-(4-chlorophenyl)-1-[2-(3,4-dihydro-6,7-dimethoxy-4,4-dimethyl-1H-2-benzopyran-1-yl)ethyl]-1,2,3,6-tetrahydropyridine.

20. A compound according to claim 16 wherein NR$_9$R$_{10}$ is 4-(1-benzimidazolyl)-piperidinyl so that the specific embodiment is 1-[1-[2-(3,4-dihydro-6,7-dimethoxy-4,4-dimethyl-1H-2-benzopyran-1-yl)ethyl]-piperidin-4-yl]-1,3-dihydro-2H-benzimidazol-2-one.

21. A compound according to claim 16 wherein NR$_9$R$_{10}$ is 6,7-dimethoxy-1,2,3,4-tetrahydroisoquinolinyl so that the specific embodiment is 2-[2-[(6,7-dimethoxy-4,4-dimethylisochroman-1-yl)ethyl]-6,7-dimethoxy-1,2,3,4-tetrahydroisoquinoline.

22. The hydrochloride salt of the compound of claim 21.

23. A compound according to claim 13 wherein (R$_1$)$_a$ is 6,7-dimethoxy, R$_2$ and R$_3$ are both methyl and n is 3.

24. A compound of claim 23 wherein (R$_1$)$_a$ is 6,7-dimethoxy; R$_2$ and R$_3$ are methyl, R$_4$ and R$_5$ are hydrogen, R$_8$ is methyl and NR$_9$R$_{10}$ is 1,2,3,6-tetrahydro-4-phenylpyridine so that the specific embodiment is 4-phenyl-1-[3-(3,4-dihydro-6,7-dimethoxy-1,4,4-trimethyl-1H-2-benzopyran-1-yl)propyl]1,2,3,6-tetrahydropyridine.

25. The monohydrochloride, hemihydrate of the compound of claim 24.

26. A compound of claim 23 wherein (R$_1$)$_a$ is 6,7-dimethoxy; R$_2$ and R$_3$ are methyl, R$_4$ and R$_5$ are hydrogen, R$_8$ is 4-fluorophenyl and NR$_9$R$_{10}$ is 1,2,3,6-tetrahydro-4-phenylpyridine so that the specific embodiment is 4-phenyl-1-[3-[1-(4-fluorophenyl)-3,4-dihydro-6,7-dimethoxy-4,4-dimethyl-1H-2-benzopyran-1-yl]propyl]-1,2,3,6-tetrahydropyridine.

27. The monohydrochloride, monohydrate of the compound of claim 26.

28. Compounds of claim 3 wherein a is two or three, R$_2$ through R$_5$ are the same or different and are selected from the group consisting of hydrogen, alkyl of one through three carbon atoms, inclusive, and cycloalkyl of four through seven carbon atoms, inclusive, when R$_2$ and R$_4$ are taken together with the carbon atoms to which they are attached.

29. Compounds of claim 28 wherein NR$_9$R$_{10}$ is selected from the group consisting of

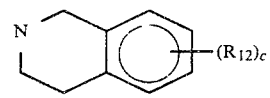

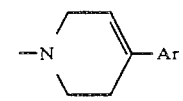

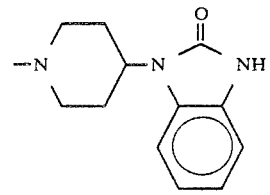

and

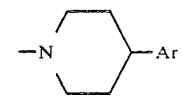

30. Compounds according to claim 29 wherein (R$_1$)$_a$ is di-alkoxy of one to three carbon atoms, inclusive; R$_2$ through R$_5$ are the same or different and are selected from the group consisting of hydrogen and alkyl of from one through three carbon atoms, inclusive, and n is three.

31. A compound of claim 30 wherein (R$_1$)$_a$ is 6,7-dimethoxy, R$_8$ is methyl and NR$_9$R$_{10}$ is 4-phenyl-1,2,3,6-tetrahydropyridinyl so that the specific embodiment is 4-phenyl-1-[3-(3,4-dihydro-6,7-dimethoxy-1-methyl-1H-2-benzopyran-1-yl)propyl]-1,2,3,6-tetrahydropyridine.

32. The monohydrochloride of the compound of claim 31.

33. A compound of claim 30 wherein (R$_1$)$_a$ is 6,7-dimethoxy; R$_2$ through R$_5$ are hydrogen, R$_8$ is methyl and NR$_9$R$_{10}$ is 4-(1,3-dihydro-2-oxo-2H-benzimidazol-1-yl)-piperidinyul so that the specific embodiment is 1-[1-[3-(3,4-dihydro-6,7-dimethoxy-1-methyl-1H-2-benzopyran-1-yl)propyl]-4-piperidinyl]-1,3-dihydro-2H-benzimidazol-2-one.

34. A compound of claim 30 wherein (R$_1$)$_a$ is 6,7-dimethoxy; R$_2$ through R$_5$ are hydrogen, R$_8$ is 4-fluorophenyl and NR$_9$R$_{10}$ is 4-phenyl-1,2,3,6-tetrahydropyridinyl, so that the specific embodiment is 4-phenyl-1-[3-(3,4-dihydro-1-(4-fluorophenyl)-6,7-dimethoxy-1H-2-benzopyran-1-yl)propyl]-1,2,3,6-tetrahydropyridine.

35. A compound of claim 30 wherein $(R_1)_a$ is 6,7-dimethoxy; $R_2$ through $R_5$ are hydrogen, $R_8$ is 4-fluorophenyl and $NR_9R_{10}$ is 4-(1,3-dihydro-2-oxo-1H-benzimidazol-1-yl)piperidinyl, so that the specific embodiment is 1-[1-[3-(3,4-dihydro-6,7-dimethoxy-1-(4-fluorophenyl)-1H-2-benzopyran-1-yl)propyl]-4-piperidinyl]-1,3-dihydro-2H-benzimidazol-2-one.

36. A compound according to claim 30 wherein $(R_1)_a$ is dialkoxy, $R_2$ and $R_3$ are hydrogen, $R_4$ and $R_5$ are lower alkyl and n is two.

37. A pharmaceutical composition wherein the therapeutically effective compound is selected from the group consisting of compounds having the formula:

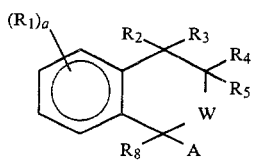

Ib wherein
$R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_5$ are the same or different and are selected from the group consisting of hydrogen, alkyl of one through three carbons, inclusive, hydroxy, alkoxy of one through three carbons, inclusive; phenyl; halo; cycloalkyl of three through six carbons when $R_2$ and $R_3$, or $R_4$ and $R_5$ are taken together with the carbon to which they are attached; cycloalkyl of four through seven carbons when $R_2$ and $R_4$ are taken together with the carbons to which they are attached; and cycloalkyl of five or six carbons, with the overall provisos that no more than one ring may be attached to any one carbon and that at least two of $R_2$ through $R_5$ are hydrogen.

$R_8$ is alkyl of one through three carbons, inclusive, hydrogen, or phenyl unsubstituted or substituted with a maximum of three substituents selected from the group consisting of alkyl of one through three carbons, inclusive, halo, alkoxy of one through three carbons, inclusive, and trihaloalkyl of one to two carbons;

W is oxygen;

and A is selected from the group consisting of:
(i) $-(CH_2)_n NR_9R_{10}$, wherein n is one to five with the proviso that when n is one or two, $R_2$ through $R_5$ cannot all be hydrogen at the same time;
(ii) $-(CH_2)_m(OCH_2CH_2)_q-NR_{21}R_{22}$, wherein m and q are each one to three, and $NR_{21}R_{22}$ is selected from the group consisting of $-NHCH_2CH_2Ar$; $NR_{21}'R_{22}'$ wherein $R_{21}'$ and $R_{22}'$ can be the same or different and are selected from the group consisting of H, alkyl of one through four carbons, inclusive, and together with the N to which they are attached form heterocyclic rings of four to six ring atoms; and

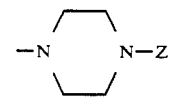

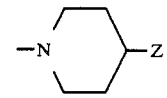

morpholino and $NR_9R_{10}$, .

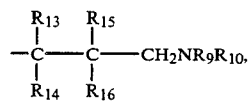

(iii)

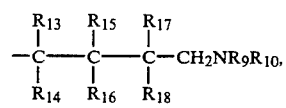

(iv)

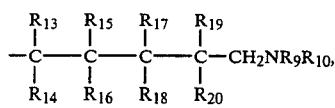

(v)

wherein $NR_9R_{10}$ is a heterocyclic amine selected from the group consisting of:

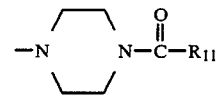

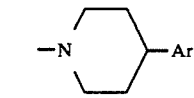

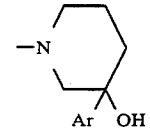

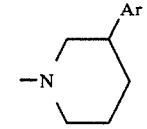

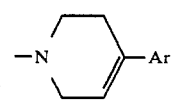

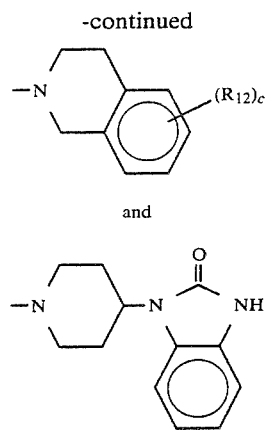

and

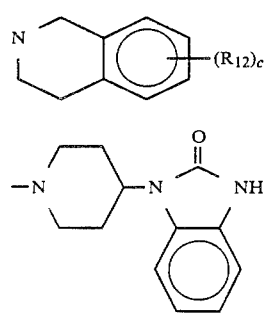

wherein
- R$_{11}$ is alkyl of one through four carbons, inclusive, 2-furyl, Ar, alkoxy of one to three carbon atoms, inclusive;
- Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive;
- R$_{12}$ is alkyl or alkoxy of one through three carbons, inclusive, hydroxy, halo, or trihalomethyl; R$_{13}$ through R$_{20}$ may be the same or different and are selected from the group consisting of hydrogen and alkyl of from 1 to 2 carbon atoms, inclusive, at least one of R$_{13}$ through R$_{20}$ when present being alkyl;
- c is zero through two;
- Ar is phenyl unsubstituted or substituted with one through three substituents selected from the group consisting of alkyl or alkoxy of one through three carbons, inclusive, hydroxy, halo, and trihaloalkyl or trihaloalkoxy of one or two carbons and pharmaceutically acceptable acid addition salts thereof.

38. Pharmaceutical compositions of claim 37 wherein a is two or three.

39. Compositions of claim 37 when A is the group —(CH$_2$)$_n$NR$_9$R$_{10}$.

40. Compositions of claim 39 wherein NR$_9$R$_{10}$ is selected from the group consisting of:

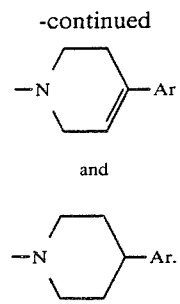

and

41. Compositions of claim 40 wherein a is two to three, and R$_2$ through R$_5$ are the same or different and are selected from the group consisting of hydrogen, alkyl of one through three carbon atoms, inclusive, and cycloalkyl of four through seven carbon atoms, inclusive, when R$_2$ and R$_4$ are taken together with the carbon atom to which they are attached, with the proviso that when R$_3$ through R$_5$ are hydrogen, R$_2$ cannot be hydrogen.

42. Compositions of claim 41 wherein (R$_1$)$_a$ is dilower alkoxy of from one to three carbon atoms, inclusive; R$_2$ and R$_3$ are both lower alkyl of from one to three carbon atoms, inclusive; and R$_4$ and R$_5$ are both hydrogen.

43. A composition according to claim 42 wherein (R$_1$)$_a$ is 6,7-dimethoxy, R$_2$ and R$_3$ are both methyl, n is 1, and NR$_9$R$_{10}$ is 4-(4-chlorophenyl)-1,2,3,6-tetrahydropyridinyl so that the therapeutically active compound is 4-(4-chlorophenyl)-1-[(3,4-dihydro-4,4-dimethyl-6,7-dimethoxy-1H-2-benzopyran-1-yl)methyl]-1,2,3,6-tetrahydropyridine.

44. A composition wherein the therapeutically active compound is the monohydrochloride salt of the compound in the composition of claim 43.

45. A composition according to claim 42 wherein (R$_1$)$_a$ is 6,7-dimethoxy, R$_2$ and R$_3$ are both methyl and n is 2.

46. A composition according to claim 45 wherein the therapeutically effective compound is selected from the group consisting of:
- 1-[2-(3,4-dihydro-6,7-dimethoxy-4,4-dimethyl-1H-2-benzopyran-1-yl)ethyl]-1,2,3,6-tetrahydro-4-phenylpyridine,
- 1-[2-(3,4-dihydro-6,7-dimethoxy-4,4-dimethyl-1H-2-benzopyran-1-yl)ethyl]-1,2,3,6-tetrahydro-4-phenylpyridine, monohydrochloride hemihydrate,
- 4-phenyl-1-[3-[1-(4-fluorophenyl)-3,4-dihydro-6,7-dimethoxy-4-methyl-1H-2-benzopyran-1-yl]propyl]-1,2,3,6-tetrahydropyridine,
- 4-phenyl-1-[3-[-(4-fluorophenyl)-3,4-dihydro-6,7-dimethoxy-4-methyl-1H-2-benzopyran-1-yl]propyl]-1,2,3,6-tetrahydropyridine monohydrohydrochloride,
- 4-(4-chlorophenyl)-1-[2(3,4-dihydro-6,7-dimethoxy-4,4-dimethyl-1H-2-benzopyran-1-yl)ethyl]-1,2,3,6-tetrahydropyridine,
- 1-[1-[2-(3,4-dihydro-6,7-dimethoxy-4,4-dimethyl-1H-2-benzopyran-1-yl)ethyl]-piperidin-4-yl-1,3-dihydro-2H-benzimidazol-2-one,
- 2-[2-[(3,4-dihydro-6,7-dimethoxy-4,4-dimethyl-1H-2-benzopyran-1-yl)ethyl]-6,7-dimethoxy-1,2,3,4-tetrahydroisoquinoline, and
- 2-[2-[(3,4-dihydro-6,7-dimethoxy-4,4-dimethyl-1H-2-benzopyran-1-yl)ethyl]-6,7-dimethoxy-1,2,3,4-tetrahydroisoquinoline.

47. A composition according to claim 42 wherein $(R_1)_a$ is 6,7-dimethoxy, $R_2$ and $R_3$ are both methyl and n is 3.

48. A composition according to claim 47 wherein the therapeutically effective compound is selected from the group consisting of:
4-phenyl-1-[3-(3,4-dihydro-6,7-dimethoxy-1,4,4-trimethyl-1H-2-benzopyran-1-yl)propyl]-1,2,3,6-tetrahydropyridine,
4-phenyl-1-[3-(3,4-dihydro-6,7-dimethoxy-1,4,4-trimethyl-1H-2-benzopyran-1-yl)propyl]-1,2,3,6-tetrahydropyridine monochloride, hemihydrate,
4-phenyl-1-[3-[1-(4-fluorophenyl)-3,4-dihydro-6,7-dimethoxy-4,4-dimethyl-1H-2-benzopyran-1-yl]propyl]-1,2,3,6-tetrahydropyridine, and
4-phenyl-1-[3-[1-(4-fluorophenyl)-3,4-dihydro-6,7-dimethoxy-4,4-dimethyl-1H-2-benzopyran-1-yl]propyl]-1,2,3,6-tetrahydropyridine monochloride monohydrate.

49. A composition of claim 42 wherein $(R_1)_a$ is 6,7-dimethoxy, $R_2$ through $R_5$ are hydrogen so that the therapeutically active compound is selected from the group consisting of:
1-[1-[3-(3,4-dihydro-6,7-dimethoxy-1-methyl-1H-2-benzopyran-1-yl)-propyl]-4-piperidinyl]-1,3-dihydro-2H-benzimidazol-2-one;
4-phenyl-1-[3-(3,4-dihydro-6,7-dimethoxy-1-methyl-1H-2-benzopyran-1-yl)propyl]-1,2,3,6-tetrahydropyridine; and
4-phenyl-1-[3-(3,4-dihydro-6,7-dimethoxy-1-methyl-1H-2-benzopyran-1-yl)propyl]-1,2,3,6-tetrahydropyridine monohydrochloride.

50. A composition according to claim 40 wherein $(R_1)_a$ is 6,7-dimethoxy; $R_2$ through $R_5$ are hydrogen, and $R_8$ is 4-fluorophenyl so that the therapeutically active compound is:
4(phenyl)-1-[3-(3,4-dihydro-1-(4-fluorophenyl)-6,7-dimethoxy-1H-2-benzopyran-1-yl)propyl]-1,2,3,6-tetrahydropyridine; and
1-[1-(3-(3,4-dihydro-6,7-dimethoxy-1-(4-fluorophenyl)-1H-2-benzopyran-1-yl)propyl]-4-piperidinyl]-1,3-dihydro-2H-benzimidazol-2-one.

51. A composition according to claim 40 wherein $(R_1)_a$ is 6,7-dimethoxy, $R_2$ and $R_3$ are both hydrogen; $R_4$ and $R_5$ are both methyl.

52. A composition according to claim 41 wherein $(R_1)_a$ is 6,7-dimethoxy, $R_3$–$R_5$ are hydrogen and $R_2$ is methyl.

53. A composition of claim 52 so that the therapeutically effective compound is selected from the group consisting of:
4-phenyl-1-[3-(3,4-dihydro-6,7-dimethoxy-1,4-dimethyl-1H-2-benzopyran-1-yl)propyl]-1,2,3,6-tetrahydropyridine,
4-phenyl-1-[2-(3,4-dihydro-6,7-dimethoxy-4-methyl-1H-2-benzopyran-1-yl)ethyl]-1,2,3,6-tetrahydropyridine monohydrochloride,
4-phenyl-1-[2-(3,4-dihydro-6,7-dimethoxy-4-methyl-1H-2-benzopyran-1-yl)ethyl]-1,2,3,6-tetrahydropyridine, and
4-phenyl-1-[3-(3,4-dihydro-6,7-dimethoxy-1,4-dimethyl-1H-2-benzopyran-1-yl)propyl)]-1,2,3,6-tetrahydropyridine monohydrochloride hemihydrate.

54. A method of treating hypertension in mammals which comprises administering to mammals an antihypertensive dose of a compound selected from the group consisting of compounds having the formula:

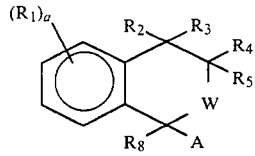

wherein
$R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_5$ are the same or different and are selected from the group consisting of hydrogen, alkyl of one through three carbons, inclusive, hydroxy, alkoxy of one through three carbons, inclusive; phenyl; halo; cycloalkyl of three through six carbons when $R_2$ and $R_3$, or $R_4$ and $R_5$ are taken together with the carbon to which they are attached; cycloalkyl of four through seven carbons when $R_2$ and $R_4$ are taken together with the carbons to which they are attached; and cycloalkyl of five or six carbons, with the overall provisos that no more than one ring may be attached to any one carbon and that at least two of $R_2$ through $R_5$ are hydrogen;

$R_8$ is alkyl of one through three carbons, inclusive, hydrogen, or phenyl unsubstituted or substituted with a maximum of three substituents selected from the group consisting of alkyl of one through three carbons, inclusive, halo, alkoxy of one through three carbons, inclusive, and trihaloalkyl of one to two carbons;

W is oxygen;

and A is selected from the group consisting of:
(i) —$(CH_2)_n NR_9 R_{10}$, wherein n is one to five with the proviso that when n is one or two, $R_2$ through $R_5$ cannot all be hydrogen at the same time;
(ii) —$(CH_2)_m(OCH_2CH_2)_q$-$NR_{21}R_{22}$, wherein m and q are each one to three, and $NR_{21}R_{22}$ is selected from the group consisting of —NNCH$_2$CH$_2$Ar; $NR_{21}'R_{22}'$ wherein $R_{21}'$ and $R_{22}'$ can be the same or different and are selected from the group consisting of H, alkyl of one through four carbons, inclusive, and together with the N to which they are attached form heterocyclic rings of four to six ring atoms; and

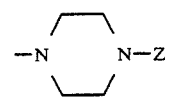

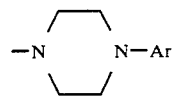

-continued

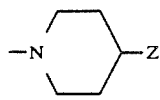

morpholino and $NR_9R_{10}$,

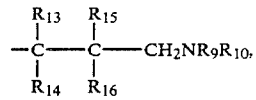 (iii)

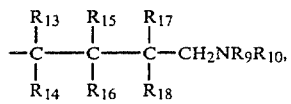 (iv)

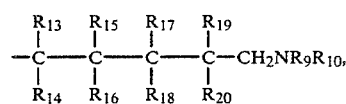 (v)

wherein $NR_9R_{10}$ is a heterocyclic amine selected from the group consisting of:

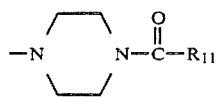

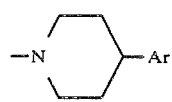

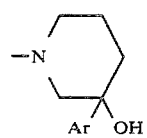

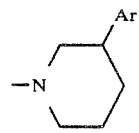

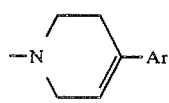

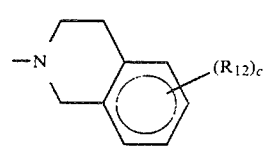

and

-continued

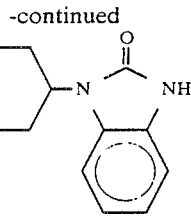

wherein
- $R_{11}$ is alkyl of one through four carbons, inclusive, 2-furyl, Ar, alkoxy of one to three carbon atoms, inclusive;
- Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive;
- $R_{12}$ is alkyl or alkoxy of one through three carbons, inclusive, hydroxy, halo, or trihalomethyl; $R_{13}$ through $R_{20}$ may be the same or different and are selected from the group consisting of hydrogen and alkyl of from 1 to 2 carbon atoms, inclusive, at least one of $R_{13}$ through $R_{20}$ when present being alkyl;
- c is zero through two;
- Ar is phenyl unsubstituted or substituted with one through three substituents selected from the group consisting of alkyl or alkoxy of one through three carbons, inclusive, hydroxy, halo, and trihaloalkyl or trihaloalkoxy of one or two carbons and pharmaceutically acceptable acid addition salts thereof.

55. A method according to claim 54 when A is the group $—(CH_2)_nNR_9R_{10}$.

56. A method according to claim 55 wherein $NR_9R_{10}$ is selected from the group consisting of:

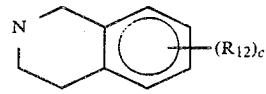

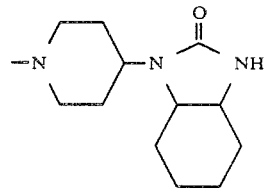

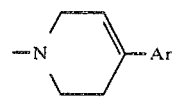

and

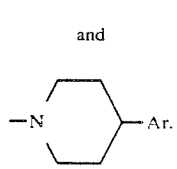

57. A method according to claim 56 wherein a is two or three, $R_2$ through $R_5$ are the same or different and are selected from the group consisting of hydrogen, alkyl of one through three carbon atoms, inclusive, and cycloalkyl of four through seven carbon atoms, inclusive, when $R_2$ and $R_4$ are taken together with the carbon atom to which they are attached, with the proviso that when $R_3$ through $R_5$ are hydrogen, $R_2$ cannot be hydrogen.

58. A method according to claim 57 wherein $(R_1)_a$ is dilower alkoxy of from one to three carbon atoms, inclusive; $R_2$ and $R_3$ are both lower alkyl of from one to three carbon atoms, inclusive; and $R_4$ and $R_5$ are both hydrogen.

59. A method according to claim 58 wherein the compound administered is selected from the group consisting of 4-(4-chlorophenyl-1-[(3,4-dihydro-6,7-dimethoxy-4,4-dimethyl-1H-2-benzopyran-1-yl)methyl]-1,2,3,6-tetrahydropyridine and the monohydrochloride acid addition salt thereof.

60. A method according to claim 58 wherein the compound administered is selected from the group consisting of:
4-(1-benzimidazolyl)-1-[(3,4-dihydro-4,4-dimethyl-6,7-dimethoxy-4,4-dimethyl-1H-2-benzopyran-1-yl)ethyl]-piperidine,
2-[2-[(3,4-dihydro-6,7-dimethoxy-4,4-dimethyl-1H-2-benzopyran-1-yl)ethyl]-6,7-dimethoxy-1,2,3,4-tetrahydroisoquinoline,
2-[2-[(3,4-dihydro-6,7-dimethoxy-4,4-dimethyl-1H-2-benzopyran-1-yl)ethyl]-6,7-dimethoxy-1,2,3,4-tetrahydroisoquinoline, hydrochloride,
1-[2-(3,4-dihydro-6,7-dimethoxy-4,4-dimethyl-1H-2-benzopyran-1-yl)ethyl]-1,2,3,6-tetrahydro-4phenylpyridine,
1-[2-(3,4-dihydro-6,7-dimethoxy-4,4-dimethyl-1H-2-benzopyran-1-yl)ethyl]-1,2,3,6-tetrahydro-4-phenylpyridine, monohydrochloride hemihydrate, and
4-(4-chlorophenyl)-1-[2-(3,4-dihydro-6,7-dimethoxy-4,4-dimethyl-1H-2-benzopyran-1-yl)ethyl]-1,2,3,6-tetrahydropyridine.

61. A method according to claim 56 wherein the compound administered is selected from the group consisting of:
4-phenyl-1-[3-(3,4-dihydro-6,7-dimethoxy-1-methyl-1H-2-benzopyran-1-yl)propyl]-1,2,3,6-tetrahydropyridine,
4-phenyl-1-[3-(3,4-dihydro-6,7-dimethoxy-1,4,4-trimethyl-1H-2-benzopyran-1-yl)propyl]-1,2,3,6-tetrahydropyridine.
4-phenyl-1-[3-[1-(4-fluorophenyl)-3,4-dihydro-6,7-dimethoxy-4,4-dimethyl-1H-2-benzopyran-1-yl]propyl]-1,2,3,6-tetrahydropyridine, and
4-phenyl-1-[3-(3,4-dihydro-6,7-dimethoxy-1,4-dimethyl-1H-2-benzopyran-1-yl)propyl]-1,2,3,6-tetrahydropyridine.

62. A method according to claim 56 wherein the compound administered is:
1-[1-[3-(3,4-dihydro-6,7-dimethoxy-1-methyl-1H-2-benzopyran-1-yl)-propyl]-4-piperidinyl]-1,3-dihydro-2H-benzimidazol-2-one.

63. A method according to claim 56 wherein the compound administered is:
4-phenyl-1-[3-(3,4-dihydro-1-(4-fluorophenyl)-6,7-dimethoxy-1H-2-benzopyran-1-yl)propyl]-1,2,3,6-tetrahydropyridine; and
1-[1-[3-(3,4-dihydro-6,7-dimethoxy-1-(4-fluorophenyl-1H-2-benzopyran-1-yl)propyl]-4-piperidinyl]-1,3-dihydro-2H-benzimidazol-2-one.

* * * * *